(12) United States Patent
Coteus et al.

(10) Patent No.: US 7,061,821 B2
(45) Date of Patent: Jun. 13, 2006

(54) ADDRESS WRAP FUNCTION FOR ADDRESSABLE MEMORY DEVICES

(75) Inventors: Paul William Coteus, Yorktown, NY (US); William Paul Hovis, Rochester, MN (US); William Wu Shen, Los Altos, CA (US); Toshiaki Kirihata, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 734 days.

(21) Appl. No.: 10/072,346

(22) Filed: Feb. 6, 2002

(65) Prior Publication Data
US 2002/0108013 A1   Aug. 8, 2002

Related U.S. Application Data

(63) Continuation-in-part of application No. 09/419,514, filed on Oct. 18, 1999, now abandoned.

(60) Provisional application No. 60/104,889, filed on Oct. 20, 1998.

(51) Int. Cl.
*G11C 11/00* (2006.01)

(52) U.S. Cl. ............................. 365/230.01; 365/189.01; 365/230.06; 365/230.08; 365/240

(58) Field of Classification Search ........... 365/230.01, 365/230.06, 230.08, 189.01, 240, 189.05
See application file for complete search history.

(56) References Cited

U.S. PATENT DOCUMENTS

| | | | |
|---|---|---|---|
| 3,810,577 A | 5/1974 | Drescher et al. ............ | 235/153 |
| 4,369,511 A | 1/1983 | Kimura et al. ............... | 371/21 |
| 4,649,475 A | 3/1987 | Scheuneman ............... | 364/200 |
| 4,926,322 A * | 5/1990 | Stimac et al. ................ | 703/23 |
| 5,440,687 A * | 8/1995 | Coleman et al. ............. | 709/236 |
| 5,742,753 A | 4/1998 | Nordsieck et al. ....... | 395/182.09 |
| 6,518,794 B1 * | 2/2003 | Coteus et al. ................ | 326/93 |
| 6,701,422 B1 * | 3/2004 | Bao ............................. | 711/201 |
| 2002/0144075 A1 * | 10/2002 | Bao ............................. | 711/201 |

FOREIGN PATENT DOCUMENTS

| | | | |
|---|---|---|---|
| FR | 002808605 A1 * | 11/2001 | |
| GB | 002282470 A * | 4/1995 | |
| JP | 409297711 A * | 11/1997 | |

OTHER PUBLICATIONS

"256Mb Double Data Rate Synchronous DRAM", IBM Brochure, 33L8026 F45424, Jan. 1999, 67 pages.
"16M x 72 2 Bank Registered DDR SDRAM Module", IBM Brochure, 19L7204 Flyer, Nov. 1998, pp. 1-8.

* cited by examiner

*Primary Examiner*—Viet Q. Nguyen
(74) *Attorney, Agent, or Firm*—Thomas A. Beck; Daniel P. Morris

(57) ABSTRACT

The invention is a selectable function that permits the address portion of data words to be separated from the storable content portion and that address portion to be used for different purposes without disturbing the stored contents in the memory array. The invention may be viewed as a command capability that permits analysis of signals for errors in such items as addresses, impedance calibration, timing, and component drift that develop in and between regions of an overall memory array.

Techniques are advanced involving data responsive selectable array circuitry modification for such operations as address correctness verification, machine timing and component drift correction purposes.

The principles are illustrated with memory systems built of Synchronous Dynamic Random Access Memory with Double Data Rate (SDRAM-DDR) elements.

12 Claims, 15 Drawing Sheets

FIG. 1

| | | | | | | | |
|---|---|---|---|---|---|---|---|
| $V_{DD}$ | $V_{DD}$ | $V_{DD}$ | 1 | 66 | $V_{SS}$ | $V_{SS}$ | $V_{SS}$ |
| NC | DQ0 | DQ0 | 2 | 65 | DQ15 | DQ7 | NC |
| $V_{DDQ}$ | $V_{DDQ}$ | $V_{DDQ}$ | 3 | 64 | $V_{SSQ}$ | $V_{SSQ}$ | $V_{SSQ}$ |
| NC | NC | DQ1 | 4 | 63 | DQ14 | NC | NC |
| DQ0 | DQ1 | DQ2 | 5 | 62 | DQ13 | DQ6 | DQ3 |
| $V_{SSQ}$ | $V_{SSQ}$ | $V_{SSQ}$ | 6 | 61 | $V_{DDQ}$ | $V_{DDQ}$ | $V_{DDQ}$ |
| NC | NC | DQ3 | 7 | 60 | DQ12 | NC | NC |
| NC | DQ2 | DQ4 | 8 | 59 | DQ11 | DQ5 | NC |
| $V_{DDQ}$ | $V_{DDQ}$ | $V_{DDQ}$ | 9 | 58 | $V_{SSQ}$ | $V_{SSQ}$ | $V_{SSQ}$ |
| NC | NC | DQ5 | 10 | 57 | DQ10 | NC | NC |
| DQ1 | DQ3 | DQ6 | 11 | 56 | DQ9 | DQ4 | DQ2 |
| $V_{SSQ}$ | $V_{SSQ}$ | $V_{SSQ}$ | 12 | 55 | $V_{DDQ}$ | $V_{DDQ}$ | $V_{DDQ}$ |
| NC | NC | DQ7 | 13 | 54 | DQ8 | NC | NC |
| NC | NC | NC | 14 | 53 | NC | NC | NC |
| $V_{DDQ}$ | $V_{DDQ}$ | $V_{DDQ}$ | 15 | 52 | $V_{SSQ}$ | $V_{SSQ}$ | $V_{SSQ}$ |
| NC | NC | LDQS | 16 | 51 | UDQS | DQS | DQS |
| NC | NC | NC | 17 | 50 | NC | NC | NC |
| $V_{DD}$ | $V_{DD}$ | $V_{DD}$ | 18 | 49 | $V_{REF}$ | $V_{REF}$ | $V_{REF}$ |
| NC | NC | NC | 19 | 48 | $V_{SS}$ | $V_{SS}$ | $V_{SS}$ |
| NC | NC | LDM | 20 | 47 | UDM | DM | DM |
| /WE | /WE | /WE | 21 | 46 | $\overline{CLK}$ | $\overline{CLK}$ | $\overline{CLK}$ |
| $\overline{CAS}$ | $\overline{CAS}$ | $\overline{CAS}$ | 22 | 45 | CLK | CLK | CLK |
| $\overline{RAS}$ | $\overline{RAS}$ | $\overline{RAS}$ | 23 | 44 | CKE | CKE | CKE |
| $\overline{CS}$ | $\overline{CS}$ | $\overline{CS}$ | 24 | 43 | NC | NC | NC |
| NC | NC | NC | 25 | 42 | A12 | A12 | A12 |
| BA0 | BA0 | BA0 | 26 | 41 | A11 | A11 | A11 |
| BA1 | BA1 | BA1 | 27 | 40 | A9 | A9 | A9 |
| A10/AP | A10/AP | A10/AP | 28 | 39 | A8 | A8 | A8 |
| A0 | A0 | A0 | 29 | 38 | A7 | A7 | A7 |
| A1 | A1 | A1 | 30 | 37 | A6 | A6 | A6 |
| A2 | A2 | A2 | 31 | 36 | A5 | A5 | A5 |
| A3 | A3 | A3 | 32 | 35 | A4 | A4 | A4 |
| $V_{DD}$ | $V_{DD}$ | $V_{DD}$ | 33 | 34 | $V_{SS}$ | $V_{SS}$ | $V_{SS}$ |

16Mb×16
8Mb×8

| Operation | CKE n-1 | CKE n | CS | RAS | CAS | WE | DM | BA0-BA1 | A10 | A0-A9, A11 | MNE | Notes |
|---|---|---|---|---|---|---|---|---|---|---|---|---|
| Device Deselect | H | X | H | X | X | X | X | X | X | X | INHBT | |
| No Operation | H | X | L | H | H | H | X | X | X | X | NOP | |
| Load Mode Register Mode or Extended Mode Register | H | X | L | L | L | L | X | OP CODE | | | MRS/EMRS | 1 |
| Row Activate | H | X | L | L | H | H | X | BS | Row Address | | ACT | 2 |
| Read | H | X | L | H | L | H | X | BS | L | Col | RD | 3 |
| Read w/ Auto Precharge | H | X | L | H | L | H | X | BS | H | Col | RAP | 3 |
| Write | H | X | L | H | L | L | V | BS | L | Col | WR | 3, 4 |
| Write w/ Auto Precharge | H | X | L | H | L | L | V | BS | H | Col | WAP | 3, 4 |
| Burst Stop | H | X | L | H | H | L | X | X | X | X | BST | 5 |
| Precharge Single Bank | H | X | L | L | H | L | X | BS | L | X | PRE | |
| Precharge All Banks | H | X | L | L | H | L | X | X | H | X | PREALL | |
| Auto Refresh | H | H | L | L | L | H | X | X | X | X | REF | 1 |
| Self Refresh Entry | H | L | L | L | L | H | X | X | X | X | SR(ENTRY) | 1 |
| Self Refresh Exit | L | H | H | X | X | X | X | X | X | X | SR(EXIT) | |
| | L | H | L | H | H | H | X | X | X | X | | |
| Power Down Mode (Entry) | H | L | H | X | X | X | X | X | X | X | PDN(ENTRY) | |
| | H | L | L | H | H | H | X | X | X | X | | |
| Power Down Mode (Exit) | L | H | X | X | X | X | X | X | X | X | PDN(EXIT) | |

1. Should be issued only after both banks are deactivated (PREALL command).
2. Should be issued only after the corresponding bank has been deactivated (PRE command).
3. Should be issued after the corresponding bank has been activated (ACT command).
4. Any valid Write cycles applied to the selected bank/row will be masked according to the DM.
5. Should be issued only during read burst cycles.

FIG. 3

ADDRESS WRAP FUNCTION FOR ADDRESSABLE MEMORY DEVICES

This Application is a Continuation in Part Application of parent application Ser. No. 09/419,514, Filed Oct. 18, 1999, now abandoned, which claims benefits of Ser. No. 60/104,889, filed Oct. 20, 1998.

Cross reference is made to application Serial No. 10/688,744 which is a contemporaneously filed Continuation in Part Application of the above identified parent of this application.

FIELD OF THE INVENTION

The invention relates to the providing of a wrap function useable in connection with an addressable random access memory that will wrap the address portion of data for additional use without disturbing the contents of the memory element and in particular to a special command or function capability that will selectably bypass the storage part of the memory assembly and pass the address portion on for use in collateral applications.

BACKGROUND

In many data processing operations the information being processed is in the form of increments or words that carry an accumulation portion that is to be stored and an identification portion that tells the memory array where to put it. As progress in the art has taken place the arrays have become huge, the housekeeping and control circuitry very complex and the stored information both large and valuable. There have long been problems with such arrays in the ever increasing speed and size environment with testing, with timing and with component drift as examples. Where the memory array is made up of received, and in the timing of when data is launched or captured. It will further be desirable to periodically re-initialize timing as components drive or where addressable devices, on coming out of a long period of inactivity, may be found to have undergone a timing change due to temperature or voltage variation.

A need is developing in the art to be able to maintain and to reestablish conditions at individual memory elements in an array without tampering with the information stored in the array.

SUMMARY OF THE INVENTION

The invention is a selectable function that permits the address portion of data words to be separated from the storable content portion and that address portion to be used for different purposes without disturbing the stored contents in the memory array. The invention may be viewed as a command capability that permits analysis of signals for errors in such items as addresses, output driver impedance calibration, timing, and component drift that develop in and between regions of an overall memory array.

A technique of testing addressing is advanced whereby information on the address bus of a memory element such as a semiconductor integrated element is routed directly to the data pins of the element and driven back to the controller of the element, so that by comparing the information that the controller sent on the address lines, to the information received on the data lines, it can be determined if there are any fails in the address or data lines, without disturbing the stored contents of the memory array.

Techniques are advanced involving data responsive selectable array circuitry modification whereby the storage portion of the array is isolated and the address portion of the data is rerouted and refunctioned for such operations as timing, verification and component drift correction purposes.

The principles are illustrated with memory systems built of Synchronous Dynamic Random Access Memory with Double Data Rate (SDRAM-DDR) elements.

BRIEF DESCRIPTION OF THE DRAWINGS

FIGS. 1–9 illustrate the application of the principles of the invention to the analysis of the integrity of address signals as they are propagated through an addressable memory array; wherein: FIGS. 1–6 illustrate the assignment of reference numerals pertaining to the invention to selected nodes of a typical standard in the art addressable memory system, in which:

FIG. 1 illustrates a basic addressable memory element such as a semiconductor integrated circuit, in a typical package such as a dual in line package, with reference numerals assigned to pins and terminals that will be involved in the illustration of the invention.

FIGS. 2A and 2B illustrate the interconnected functional elements of a, typical in the art, Double Data Rate Synchronous Dynamic Random Access Memory (SDRAM-DDR), with reference numerals assigned to elements pertaining to the invention.

FIG. 3 is an illustration of a function truth table for a typical in the art SDRAM-DDR, such as illustrated in FIGS. 2A and 2B.

FIG. 6 is a perspective illustration of the arrangement of the SDRAM-DDR type memory cards in a typical in the art computer system as illustrated in FIGS. 1–5 with reference numerals added pertaining to this invention. FIGS. 7–9 are structure, flow and timing diagrams illustrating the by pass implementation of the invention, wherein:

FIG. 8 illustrates the information flow of the invention in a computer system such as that of FIG. 6 with reference numerals pertaining to the invention.

FIG. 9 illustrates in a timing diagram the performance when the system is in the wrap function or echo function mode of the invention with reference numerals pertaining to the invention.

DESCRIPTION OF THE INVENTION

Figure 2A:
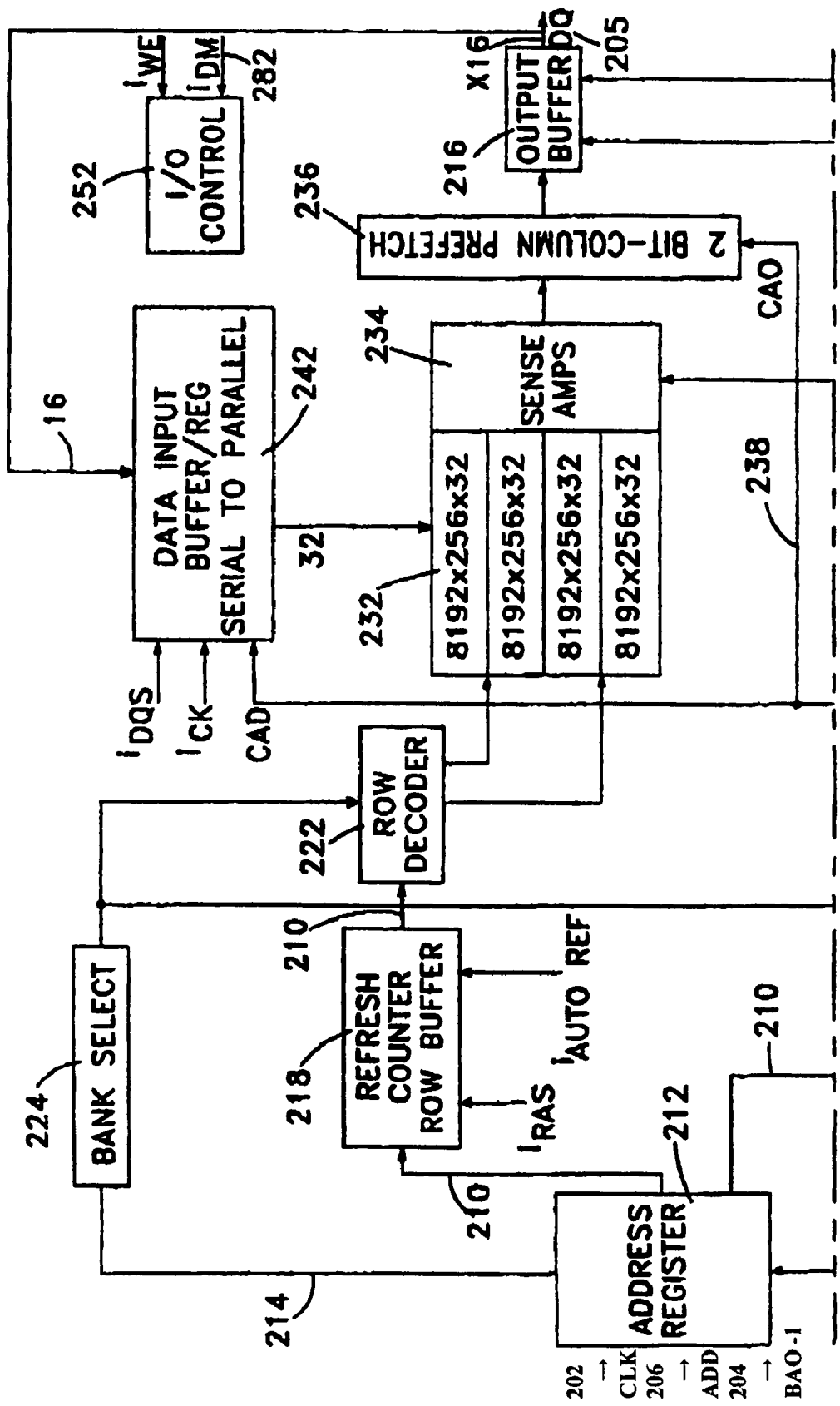

The selectable function of the invention that permits the address portion of data to be separated from the storable content portion so that that address portion can be used for different purposes, can be implemented in many ways such as through hardware additions, software instructions and combinations thereof. The implementations fall into groups where the storage arrays are by passed and groups where the storage arrays are isolated and the address data is rerouted and used for other purposes. In both types of groups the memory content remains undisturbed. The invention may be viewed as being a command or wrap function that permits analysis, verification and correction of variations in such data paths as address, timing, impedance variation and component drift in addressable memory assemblies without disturbing the content of the actual stored data in the memory assembly. The memory assembly is made up of an interrelated arrangement of storage and control entities. In FIGS. 1–6 there is illustrated a typical Dynamic Random Access Memory (DRAM) made up of components and data paths and controls assembled on standard in the art packaging on cards and boards. This invention is directed toward providing a capability for analyzing critical types of data paths and providing correction so as to keep the interrelationship within proper limits without disturbing data that may be stored in memory.

Referring to FIGS. 1 to 6, in FIG. 1 there is shown a basic addressable memory element such as a semiconductor integrated circuit, in a typical package such as a dual in line package, with reference numerals assigned to pins and terminals that will be involved in the illustration of the invention. In FIG. 1 the semiconductor integrated circuit element is labelled 101 and all signal pins are listed. There are address pins A0–A12, labelled 102, for addressing the memory contents by row and column. There are banks of select pins BA0–BA1, labelled 103, for addressing one of the 4 internal memory banks, command pins RAS, CAS, WE, and CS, labelled 104, which respectively refer to row address, column address, write enable, and chip select. There is a differential clock CLK CLK/ pair, labelled 105, for synchronizing operations within the chip to a system clock, and a clock enable pin CLE, labelled 106, for enabling and disabling the clock. There are 4, 8, or 16 data ports, shown in FIG. 1 as DQ0–DQ15 depending on the data width of the chip, with data strobes UDQS, LDQS, labelled 107, one for each 8 data bits. The data ports are used to send READ information data, or receive WRITE information data. The strobe is driven with the data on a read and receive operation, serving the function of a clock, with data present on both rising and falling edges of the strobe pulse. There are also voltage supply pins VDD and VSS for the internal circuitry, and I/O voltage supply pins VDDQ and VSSQ for the data and strobe pins, and a reference voltage Vref pin for receiving data.

Figure 2:
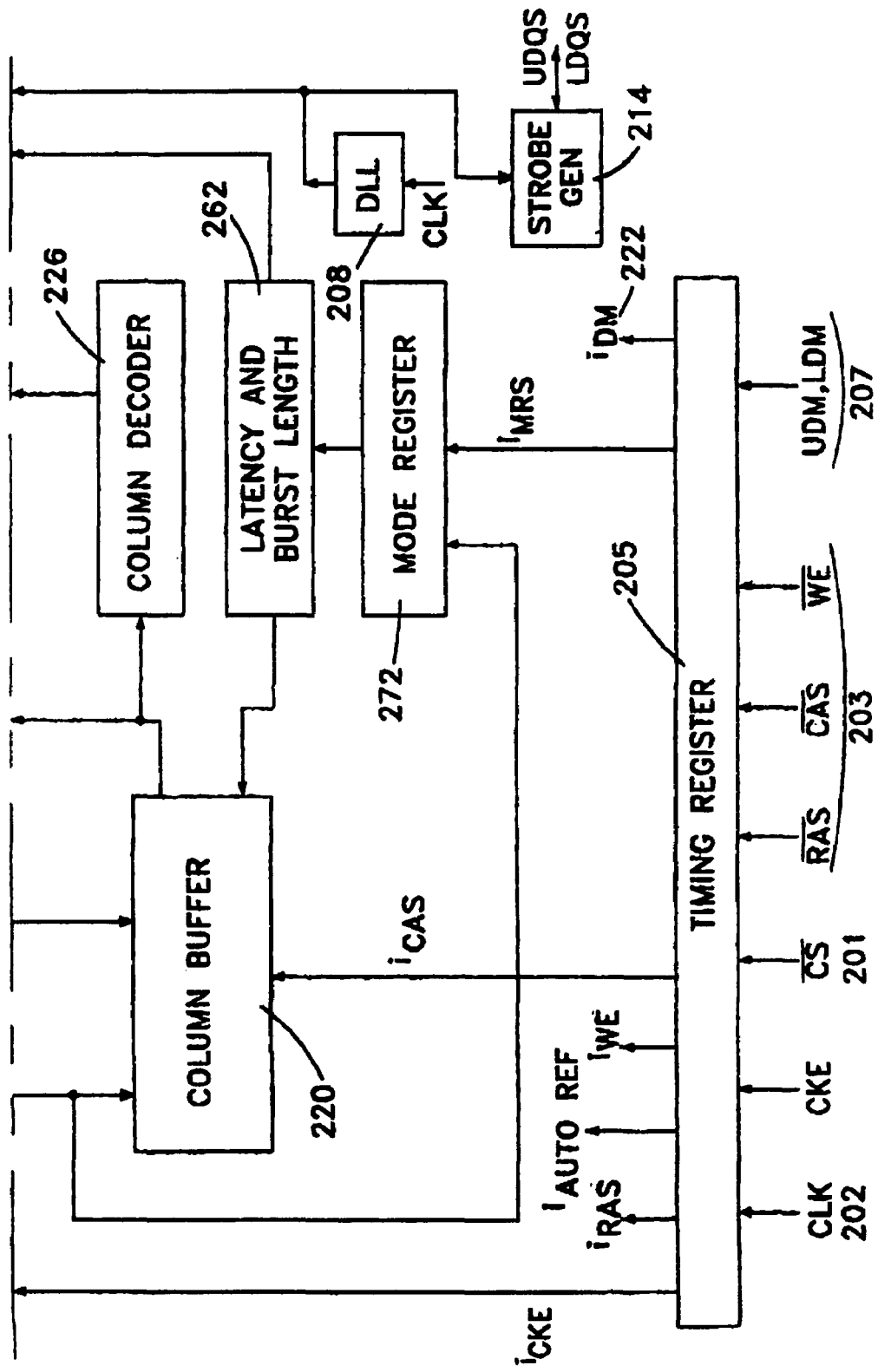
Figure 4A:
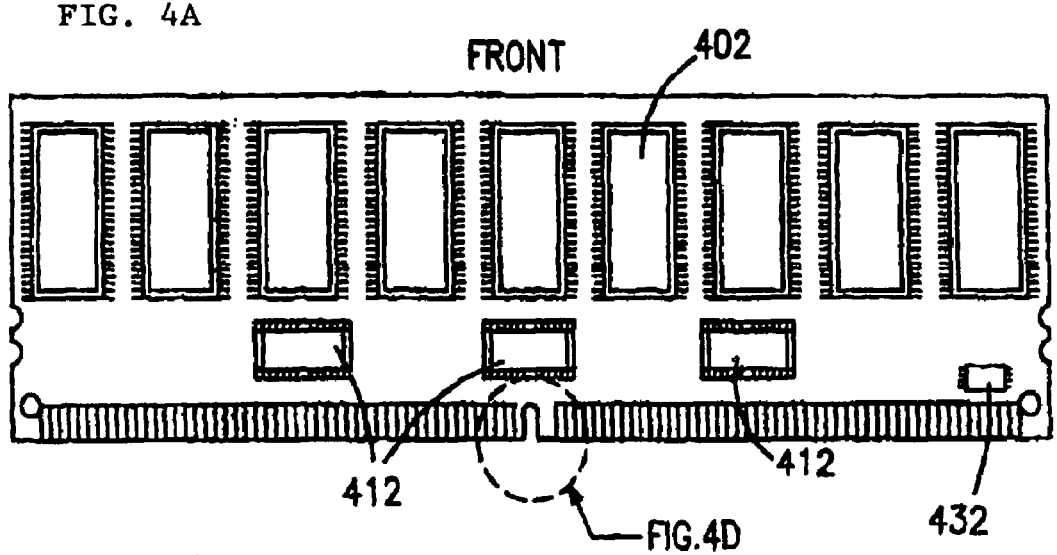
FIGS. 4A–4D are illustrations of a layout on a subassembly member or card of a two memory bank SDRAM-DDR of the type illustrated in FIGS. 1–3 with reference numerals added pertaining to this invention.
Figure 4B:
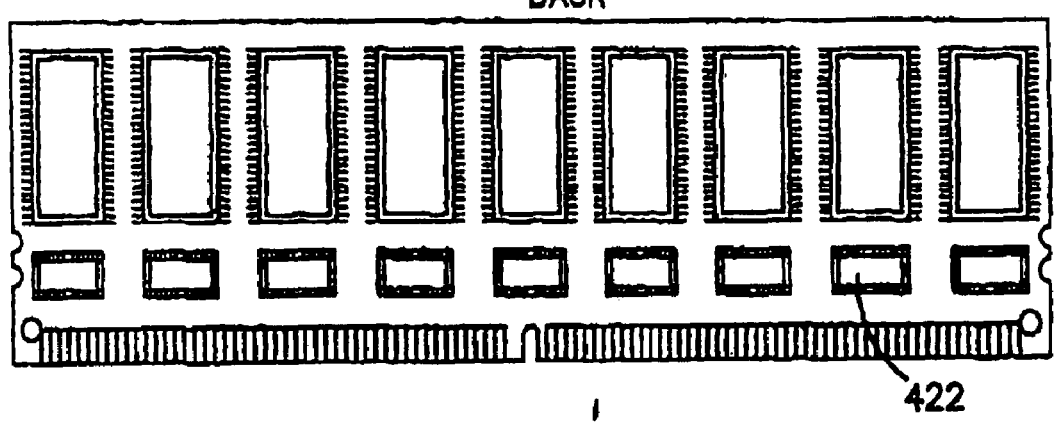
Figure 4C:
Figure 4D:
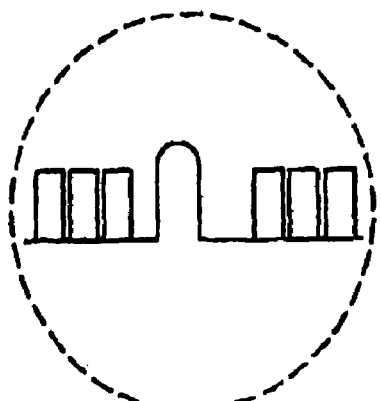
Figure 5A:
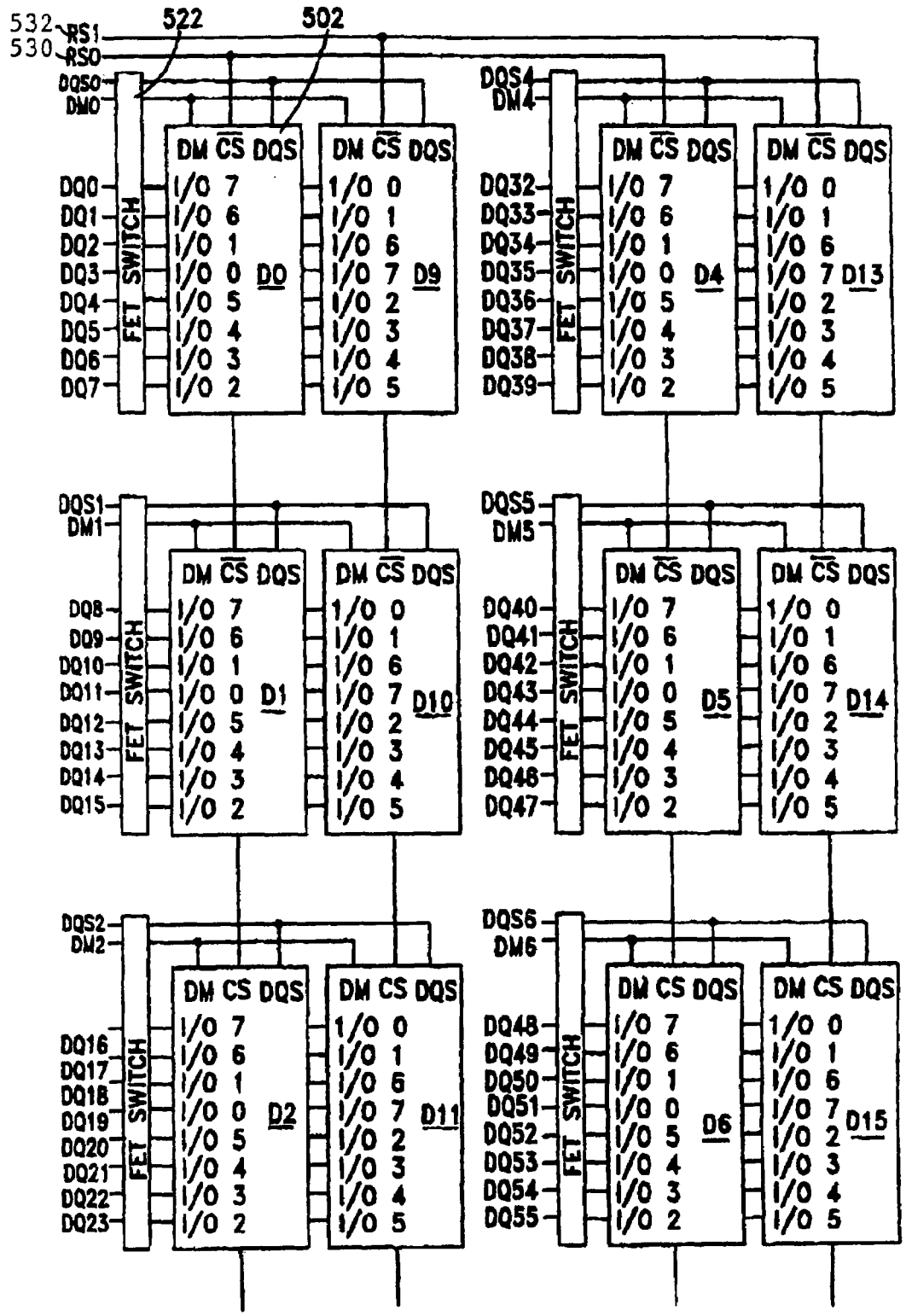
FIGS. 5A–5D are an illustration of a schematic diagram of a typical in the art two memory bank SDRAM-DDR of the type illustrated in FIGS. 1–4 with reference numerals added pertaining to this invention.
Figure 5B:
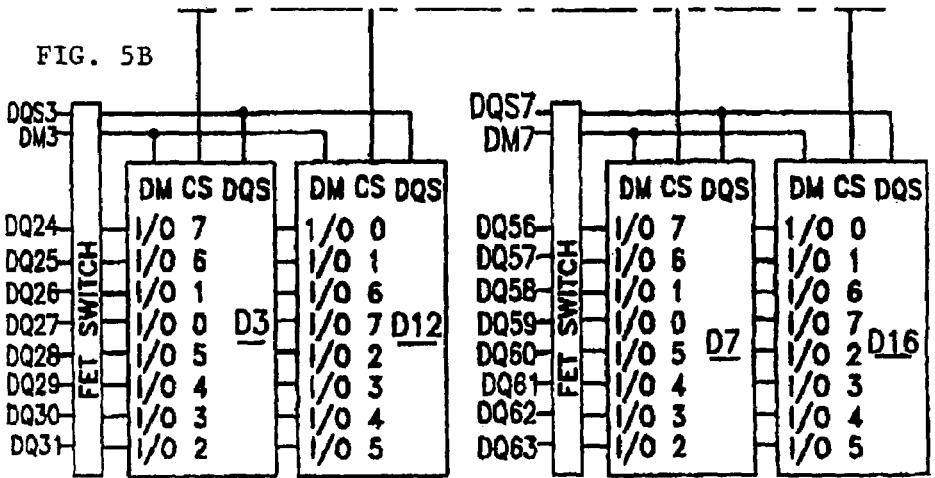
Figure 5C:
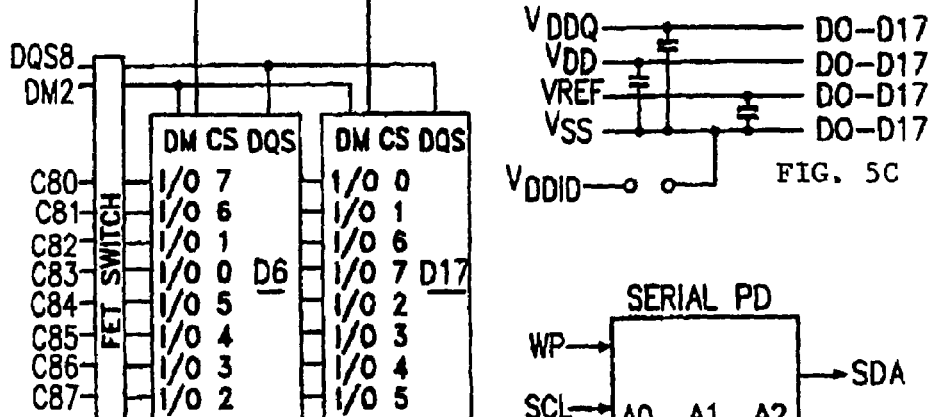
Figure 5E:
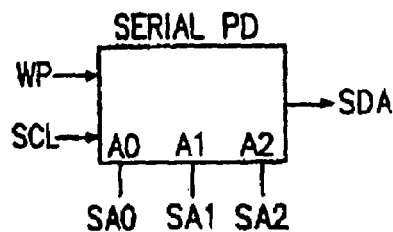
Figure 5D:
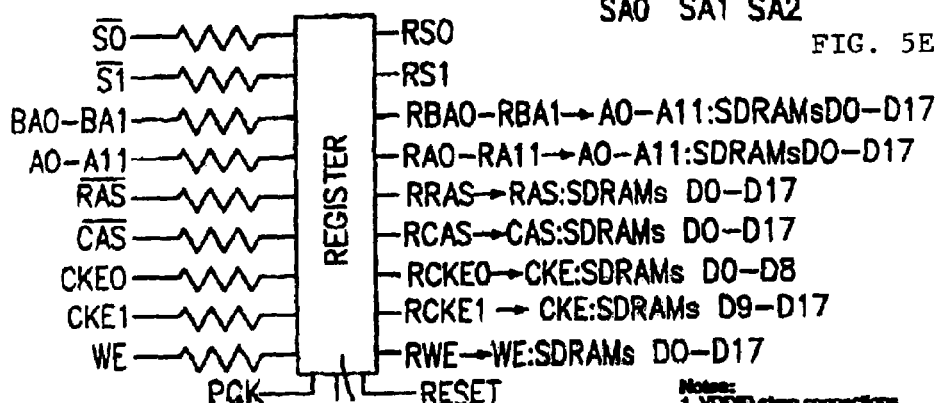

FIG. 1 and FIG. 2 together illustrate the interconnected functional elements of a, typical in the art, Double Data Rate Synchronous Dynamic Random Access Memory (SDRAM-DDR), with reference numerals assigned to elements pertaining to the invention and together describe an addressable semiconductor device with an address and data port, which are essential data path locations in analysis of address accuracy.

In FIG. 2, a functional diagram is shown with connections to the major parts of the Random Access Memory (RAM) device. In FIG. 2, the clock is labelled (202), it is used in this instance, to receive in the address register, labelled (212), the address, labelled (206), and the memory bank address, labelled (204). In the timing register, labelled (205), the clock (202), is received along with the chip select command, labelled (201), and the ras, cas, and we commands, labelled (203). The clock signal, delayed by a delay locked loop, labelled (208), is used to drive a data strobe generator, labelled (214), in synchronizing the output data in a read operation through the output buffer, labelled (216), such that the clock and output data are in phase.

The timing register (205) is used to determine if the address bus, labelled (210), is directed to the row buffer, labelled (218), or to the column buffer, labelled (220). A bank activate, or row selection, would occur, for example, if the chip select (201) is low, and the ras is low, and the cas is high of (203); whereas a read or write or column selection, would occur, for example, if chip select (201) is low, and ras, and cas of (203) are both low.

In FIG. 3 there is an illustration of a function truth table which indicates the conditions in the DRAM.

Returning to FIG. 2, in a condition where the row is selected then the row address is decoded by the row decoder, labelled (222), the 13 address bits would specify one of 8192 possible rows in the data arrays labelled (232). There are 4 possible arrays shown in the FIG. 2 example, the desired one to be activated will be determined by a bank selector, labelled (224).

An important point to be noted with respect to the problems addressed by this invention is that, at this point, all address information, even if some inaccuracy is present, will contain sufficient information to be executed and will and appear to the memory apparatus as being valid. Thus, if there were to be an error on a received address, caused for example by a broken connection in the path between the device creating the address which would be the memory controller of FIG. 6, to be later described, and the memory device, the transmitted data would still be sent or received, and the error could be difficult to detect.

Returning again to FIGS. 2A and 2B, once a row has been selected, then the desired column, or columns of that row are selected, the data in the column buffer is then sent to the column decoder, labelled (226), which selects the required data bits from the final sense amplifiers (234). Since this is a double data rate memory, which in essence means that 2 data bits are to be transferred per DQ port, for every clock cycle, 2 data bits then must be fetched from the arrays 232 for every clock cycle. Which of these 2 bits is output first is determined by the 2 bit column prefetch unit, labelled (236), by inspection of the low order column address CA0, labelled (238). The CA0 (238) is also routed to the data input buffer labelled (242), which receives data in a write operation from the DQ pins, labelled (250), which permits determining that the two bits received on that clock cycle go to the proper address.

The role of CA0(238) is important in the address analysis aspect of the invention in that it is a location where address information is used in the data portion of the chip. In this invention a goal is to bring all of the address and command information, or as much of it as possible, to the data portion of the chip, providing the ability for the information received on the address and command lines to be sent out the data lines, so that a memory controller can check if the address and command it sent to the addressable device, was actually received correctly, by inspection of the data lines. This invention will not affect the contents of the RAM or the normal operation of the addressable device, as the invention will provide a separate bus.

Continuing to refer to FIG. 2, on a read operation, data from the 2-bit column prefetch unit (236) are driven to the output buffers labelled (216) and out the data ports labelled DQ and (250). At the same time the data strobes UDQS and LDQS at element labelled(214) are driven. The receiving device can use these strobes in the same manner as the RAM to register the data. The timing register controls when the data is driven through the I/O control unit, labelled (252). The data is driven as a burst, unit labelled (262), determines when the burst is over and signals the output buffer. The number of cycles between the read command and the data (the latency) is programmable as is the length of the burst, the programming is done by a memory controller or other external device by using a special command (mode register write) by proper selection of the commands, cke, cs, ras, cas, and we, that enter the timing register (205); the command itself is contained in the address field. Thus the address path labelled (210) is directed also to the mode register labelled (272), which decodes the instructions during initialization and determines, among other things, the burst length and latency.

This invention makes use of a mode register for memory devices where available and a special command is provided to direct the address bus to the data bus in other words to achieve the address wrap function.

The same address wrap function may be provided in other devices without a mode register by programming.

Returning to FIG. 2, similarly if data is being written to the RAM, data received by the input buffer (242) is directed to the selected row and column of the array labelled (232). The data strobes UDQS and LDQS are used to clock in the data, that is, on rising edge of strobe one datum is registered from the receiver and on the falling edge a second datum, hence the double data rate.

With respect to the problem being addressed, again all addresses appear to be valid. If there was an error on a received address, due to example a broken connection in the path between the device creating the address, such as the memory controller, to be discussed in connection with FIG. 6, and the memory device, the data to be stored in the memory would still be written, just to the wrong address. This can overwrite otherwise correct data and can have serious consequences in many computers.

It is possible to mask, or block, certain data from being written and in fact on some earlier memory devices certain data could be masked for both a read and a write operation. With this invention, the mask operation is enabled through use of the mask pins, UDM and LDM, labelled (207). UDM masks signals at terminal DQ8-15 and LDM masks signals at terminal DQ0-7, from being written to the array. The operation is through the generation of the iDM signal labelled (282), by the timing register (205), and introduced into the I/O control (252).

Referring to FIG. 3, which is an illustration of a function truth table for a typical in the art SDRAM-DDR, such as illustrated in FIG. 2.and which shows the commands that can be created for the SDRAM-DDR memory devices through use of the commands cke, cs, ras, cas, we, and dm, and the address. The read and write commands have been discussed above, the other commands are not important for this invention but are shown for completeness.

FIG. 4 is an illustration of a layout on a subassembly member or card of a two memory bank SDRAM-DDR of the type illustrated in FIGS. 1–3 with reference numerals added pertaining to this invention. The layout of FIG. 4 is of a typical 128 Megabyte (MB) 184 pin registered 8-byte Dual Inline Memory Module (DIMM) which uses 18, 64 Mb (megabit) SDRAM-DDR devices, labelled (402). The 64 Mb devices are very similar to the standard 256 Mb devices, but with ¼ the capacity and thus 1 fewer address line will be involved. This DIMM is shown as an example of a collection of addressable devices with a common address bus. There will be many card constructions involving capabilities that will not be involved nor do they affect this invention. Such capabilities are redrive functions labelled (412). There are also data switches labelled (422) shown on the backside, such data switches are used to isolate the memory devices on this DIMM from other DIMMs when multiple DIMMs share a common data bus. The presence or absence of these data switches has no bearing on the address wrap command of this invention. Some card constructions have small EEPROMs labelled (432) which contains descriptive information about the DIMM. The presence or absence of this EEPROM has no bearing on the address wrap command of this invention.

FIG. 5 is an illustration showing how a typical two banks of memory devices on front and back of a card as shown in FIG. 4 are wired together. Referring to FIG. 5, the SDRAM-DDR devices are labelled (502), the address registers are labelled (512), and the data switches are labelled (522). The address bus to all RAMs is shared. Also the data bus between the 9 RAMs in the front of the DIMM of FIG. 4 is shared with the 9 RAMs on the back of the DIMM.

Figure 6:
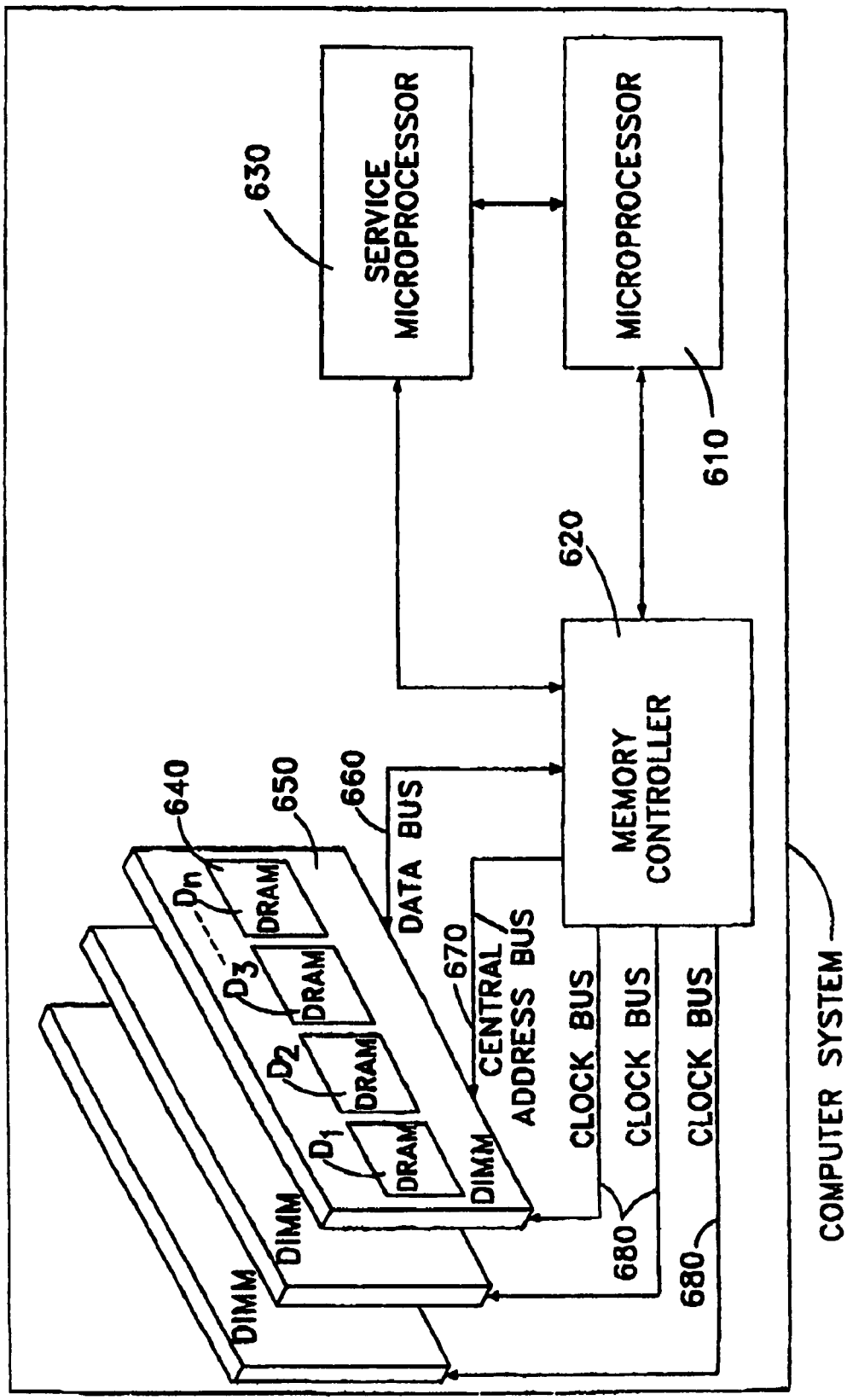

In FIG. 6 there is shown a perspective illustration of the arrangement of the SDRAM-DDR type memory cards in a typical in the art computer system as has been discussed in connection with FIGS. 1–5 with reference numerals added pertaining to this invention.

Referring to FIG. 6 there is shown a high level schematic of the memory and processor sections of a computer system. There is a processor or processors called microprocessors and labelled (610). The processor is connected to a memory controller labelled (620). In some constructions the processor and memory controller may be in the same semiconductor integrated circuit device. There is a service processor labelled (630), for providing such functions as system initialization and error processing. Again the service processor may exist with the processor, or the service processor function can be a part of the processor design. A distinction is made between processor and service processor in this discussion to facilitate explaining data being entered and data that exists in the memory in application of the address wrap function of the invention. The memory controller controls the addressable memory devices labelled (640), which could be SDRAM-DDR memory devices as in FIGS. 1 and 2, in this case shown on memory cards labelled (650) as is typical in the industry at this time, examples of which have been described in connection with FIGS. 4 and 5. The memory controller (620) receives (reads) or sends (writes) data to the memory through the data bus labelled (660). The controls tell the RAM to read or be written to through the cntrl/address bus labelled (670). While separate data busses and cntrl/address busses, may go to each DIMM, or DRAM or they can be made common, the wrap function of the invention would apply.

It is now common in the industry to have addresses, commands, and data referenced to a clock. The clock can come from a separate chip which synchronizes all components, or, in the case of SDRAM-DDR, or other high speed devices, the practice of sending the clock with the address, command, and data (source synchronous design), is being practiced in the industry. In FIG. 6 the memory controller (620) is shown with separate clock busses labelled (680). How clocking is done is not important for this invention, what is important is that the address wrap, when it occurs, follows the same timing as normal operations.

There is and have been some problems with systems such as those described in FIGS. 1–6, which are addressed by the additional command capability provided with this invention.

One problem is that all addresses to the memory contain valid information. If there is some malfunction in the memory assembly, such as a wiring break, data is accessed but it is not the correct data. Thus it is difficult to know if an address has been properly received. As bus speeds increase, this problem becomes more evident. At the present state of the art, the approach used in testing the memory assembly to determine if addresses are being properly received is by alternatively writing and reading certain data patterns into the RAM at different locations, but this however takes a large number of data transfers to perform and it destroys the contents of the memory. There may be many reasons where it is not desirable to have to destroy the contents of a memory. In accordance with the invention a means of testing the address bus is provided that is fast, and does not destroy the contents of memory.

Another problem is that progress in the art will require signaling techniques that involve adjustments in the timing of when data is launched or captured. In systems such as shown in FIG. 6, the speeds of the address and data busses can become very fast, and the detailed timing of the clock with respect to the address/command, and the data strobe with respect to the data becomes more stringent. It would be desirable to be able to periodically re-initialize such busses.

A further problem may be encountered with high speed DRAMs or other addressable memory assemblies in coming out of a long period of inactivity that timing changes may be encountered due to temperature or voltage variation. It is desirable to have a means of re-establishing timing between the addressable device and the controlling device, without accessing the memory.

In accordance with the invention solutions to these problems are achieved by providing an additional mode function called address wrap, or address echo, which can be accessed under control of a memory controller or a service processor, such as shown in FIG. 6. The purpose of the address wrap or address echo capability of the invention is to provide a bypass of the address information directly to the output where it can be evaluated without interfering with the memory contents.

Figure 7A:
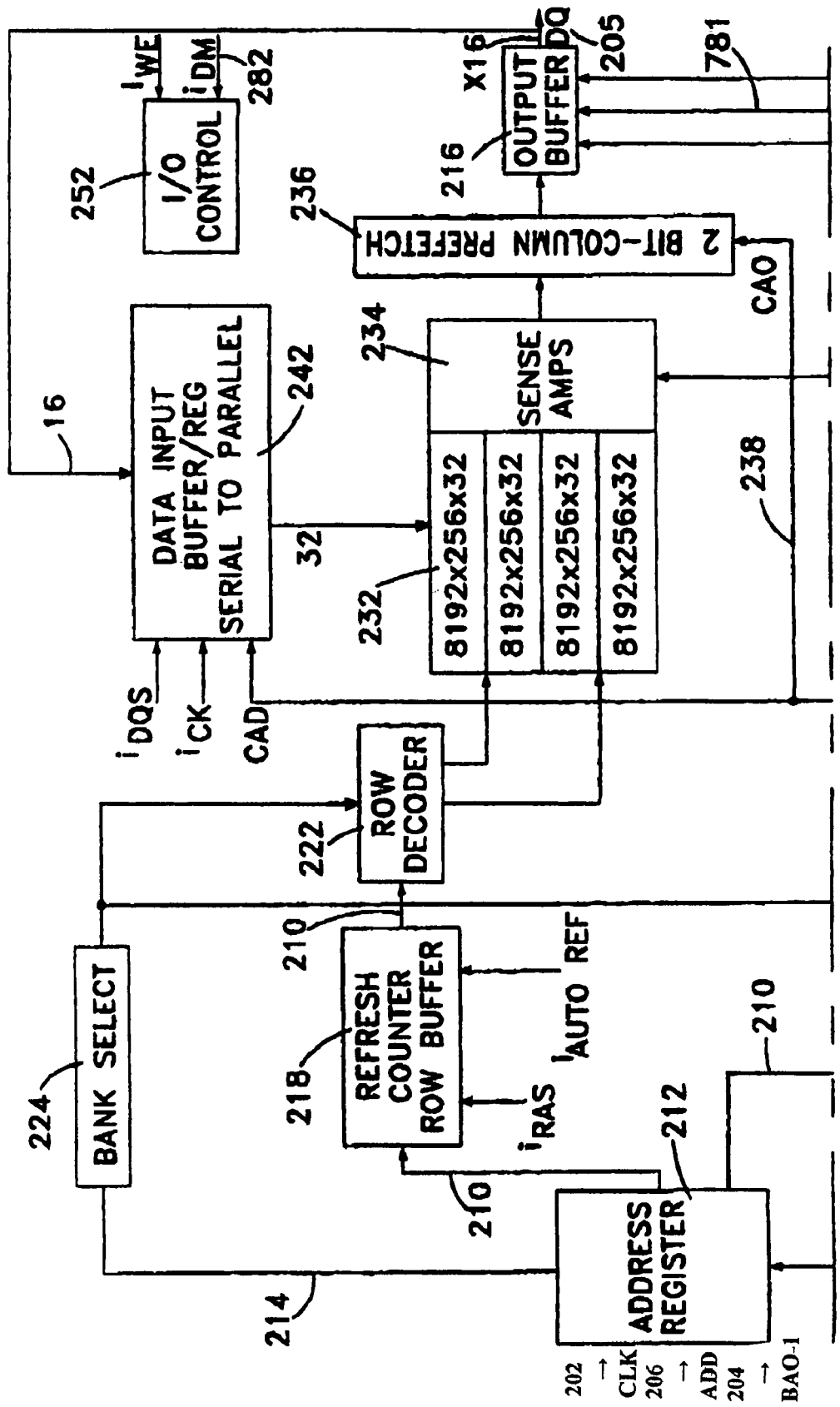
FIGS. 7A and 7B illustrate a bypass circuitry capability within the functional diagram of FIG. 2 conveying address and data port information with reference numerals pertaining to the invention.
Figure 7B:
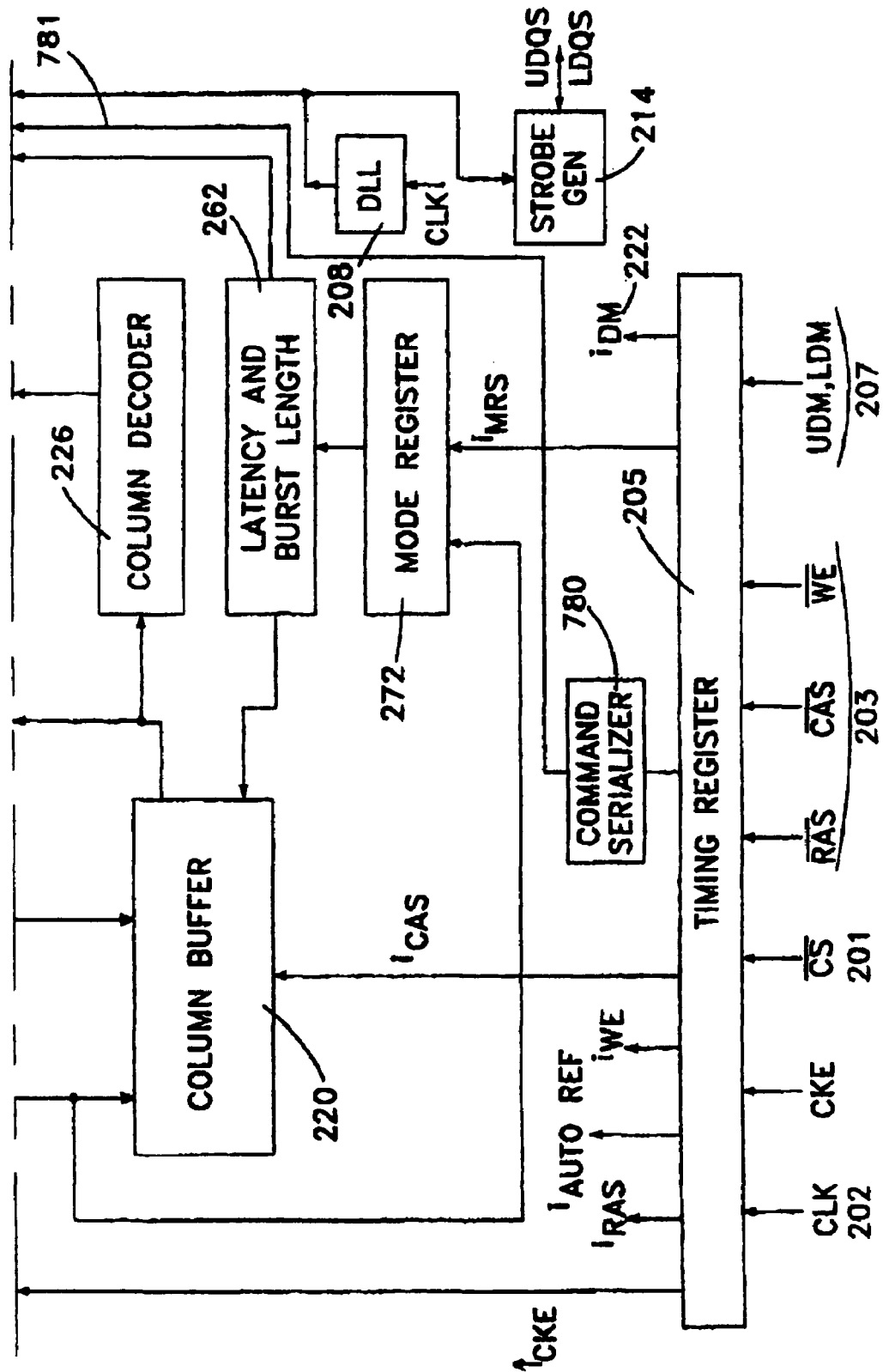

The following is an illustrative implementation. One way to control the function is to provide a command to the mode register of the addressable device, such as shown as element 272 in FIG. 2. Synchronous DRAMs use a mode register, and clock doubled synchronous DRAMs (SDRAM-DDR) have both a mode register, element 272 in FIG. 2, and an extended mode register, known in the art as an (EMR), not separately shown in FIG. 2. Address pins A4 are shown in FIG. 1. The mode bits A4 in the EMR of SDRAM-DDR are useable when assigned 0=no address echo mode and 1=address echo mode. Referring to FIGS. 7A and 7B there is illustrated a bypass circuitry capability within the functional diagram of FIG. 2 that conveys address and data port information with reference numerals pertaining to the invention. In FIGS. 7A and 7B an address serializer labelled (770), takes address information from the address register 212 and conveys it on channel labelled (771) directly to the output buffer 216 and a command serializer labelled (780) takes command information from the timing register 205 and conveys it on channel labelled (781) to the output buffer 216.

Figure 8:
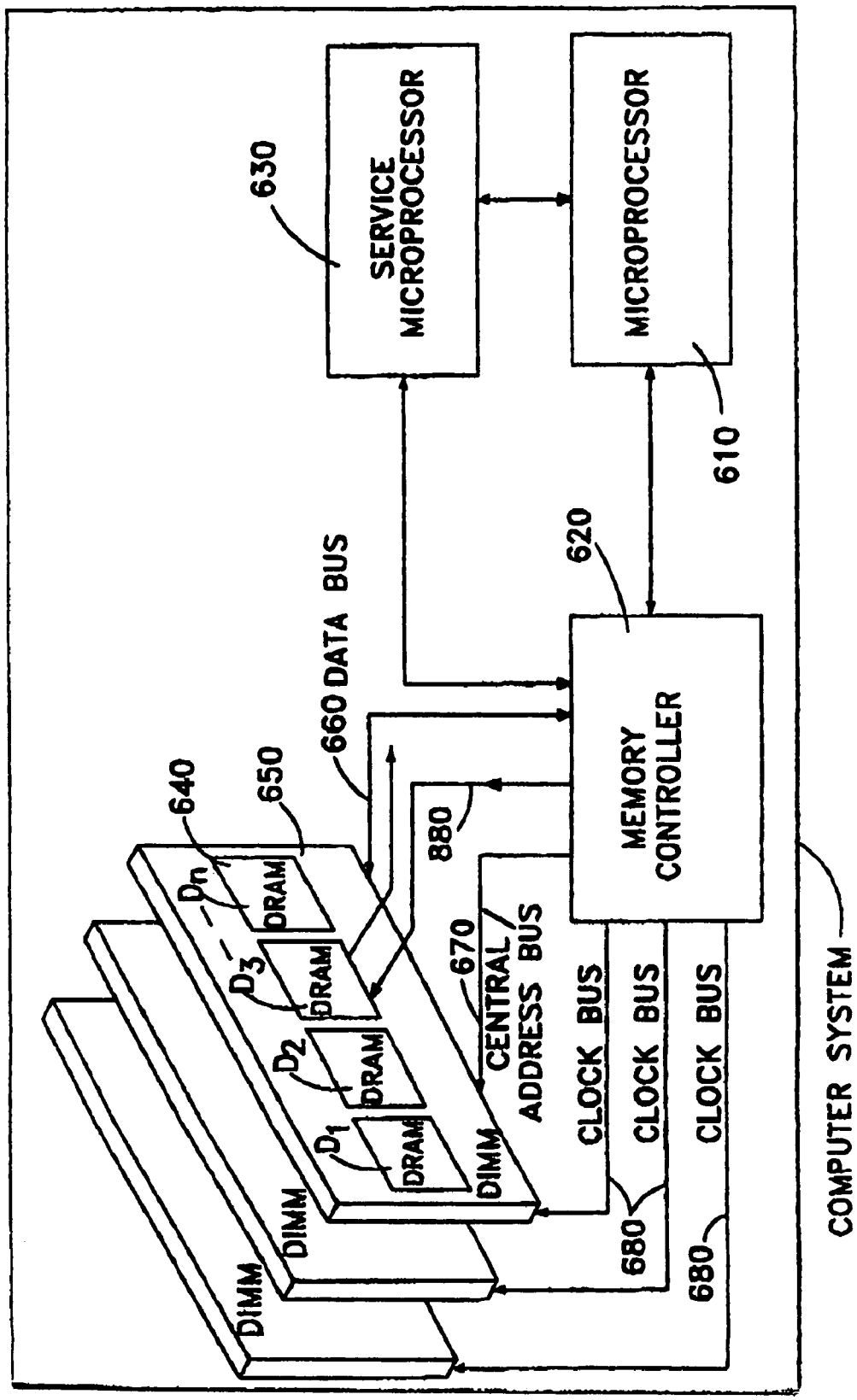
Figure 9:
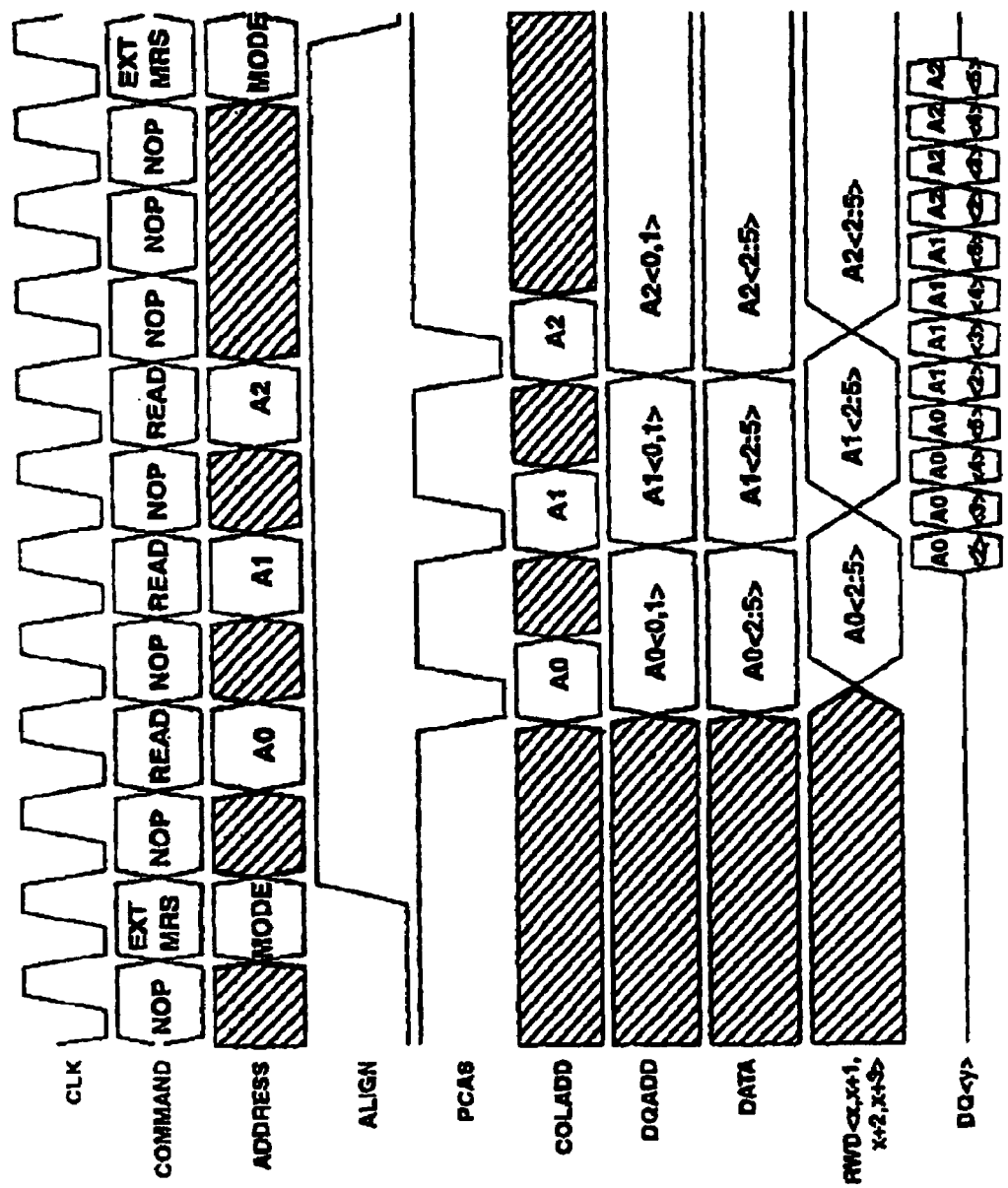

Referring to FIG. 8 there is illustrated the information flow of the invention in a computer system such as that of FIG. 6 wherein the information path labelled (880) takes a control signal from the memory controller 620 to a selected one of the DRAMs 640 on the card 650 and takes the output address information from the output buffer of the selected DRAM to an evaluation location not shown. Referring to FIG. 9 there is illustrated a timing diagram of the performance when the system is in the wrap function or echo function mode of the invention. Addresses and commands on the address/command bus show up several cycles later on the data bus. There are no new signals. On cycle n+2, starting from all DQ pins on the same side of the package, serially readout of the address and control pins located on the same side of the package as presented to the DRAM on cycle n. The order is in ascending pin number for signals located on the side of the package containing pin 1, and is descending pin numbers for the other side of the package. The serial readout should be the same frequency as read data, and obey the same launch and hold time specifications, with the same driver impedance. The serial readout terminates after 8 cycles (16 possible datum), and the data drivers are disabled. One cycle later a new command may be taken. This method is designed to provide the value of the address and control lines all output from the data lines, allowing the controlling device to sense if the sent address (or control) matches the received address (or control). If there is a discrepancy, either the address line is bad, or the data line. The difference can be determined by more complicated functions, for example alternating the order of address readout every other cycle. Other methods are of course possible to achieve different purposes. For example all address lines latched on cycle n could be output through all data lines on cycle n+2. Similarly there could be different number of cycles (1, 2, 3 etc.) between address latch and data output.

The preferred arrangement for simplicity is to have the timing for the address echo function of the invention be the same as a normal read timing of the memory assembly. This is best for the controller and the RAM, as it preserves the natural timings for normal reads and writes. The address could be serialized, and output as a serial stream of addresses commands in other words of known patterns, out of one or more data lines. All methods will produce the required information. That is, the value of the address and control lines will be output from the data lines, allowing the controlling device to sense if the sent address (or control) matches the received address (or control). If there is a discrepancy, either the address line is bad, or the data line. The difference can be determined by more complicated functions, for example alternating the order of address readout every other cycle. The EMR can be written at slow speed to improve the chance of a success in the event of a high speed address line problem. To the extent that some of the lines to be tested are required to write the EMR, the test is incomplete. However, failure to enter the address echo mode is itself an indication of address line failure.

An alternative way to invoke the address echo function of the invention is that, referring to FIG. 3, the SDRAM-DDR function truth table, there is room to define a new command. For example, it could be required that A10, the auto-precharge pin, be used with the burst stop command to create a new command. When A10 is low then the burst stop command acts as before, but when it is high it means the new command, the address wrap or address echo function of this invention. When this new command is given then all addresses and commands are wrapped to the data. There are two readily useable applications for this new command technique.

The first is to test address busses. On the memory tester, or in a separate computer system, a copy of the mode register of the device is written and the controller or tester programmed to compare the driven address to the received data. If they do not agree, there is a fault. The test is fast, it does not disturb the contents of memory, and thus it can be performed at any time.

The second is to tune the timing of the assembly to allow high speed operation of address and data busses. On the memory tester, or in a separate computer system, a copy of the mode register of the device is written and the controller or tester programmed to compare the driven address to the received data. If the data is not received correctly, it might be a broken contact or it might be that the timing relation between address and clock (or data and strobe) is not optimized. For example in a SDRAM-DDR, the controller must align the data strobe which is driven in phase with the data, to the center of the data pulse so as to be insensitive to changes in timing. It is very difficult to know where the center of the data pulse is. The controller can scan the strobe in time with respect to the data, and note when the data fails because the strobe is too early and when the read fails because the strobe is too late. All that is required for this test is that the controller know the data pattern that is to be read. Thus, the address echo or wrap function of the invention allows any data pattern to be sent and then read, in analysis and verification without disturbing the contents of memory.

The invention provides substantial advantages in connection with the timing in dynamic random access memory arrays (DRAMS) which are illustrated in connection with FIGS. 10–12.

Figure 10:
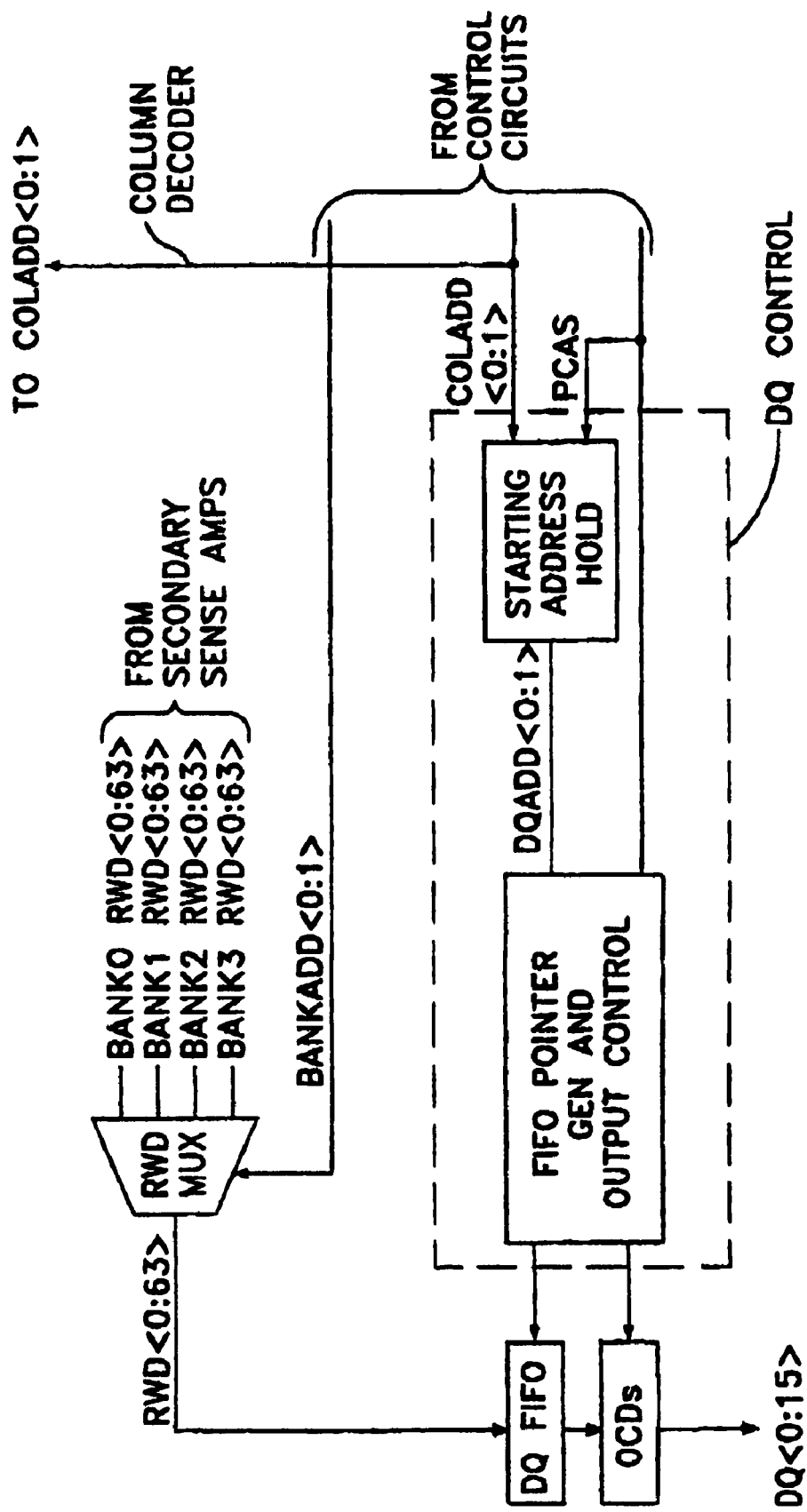
FIG. 10 is a block diagram illustrating a typical timing control data path in a DRAM assembly.

Referring to FIG. 10 a depiction is provided of the data path. The example data path has four data array banks with the read/write data (RWD) multiplexed onto a common data bus. During a read operation the signal PCAS is pulsed low while a column address supplied by the memory controller is simultaneously presented on the internal COLADD bus. Within the column access time of the array, the RWD bus will be driven with the data to be output by the OCDs onto the DQ bus. In architecture of the prefetch type this data is first serialized at the FIFO latches using input and output pointers. In this type of situation, if the COLADD bus is not guaranteed until the end of the read cycle, then the starting address must be held until needed to generate the outpot pointers.

Figure 11:
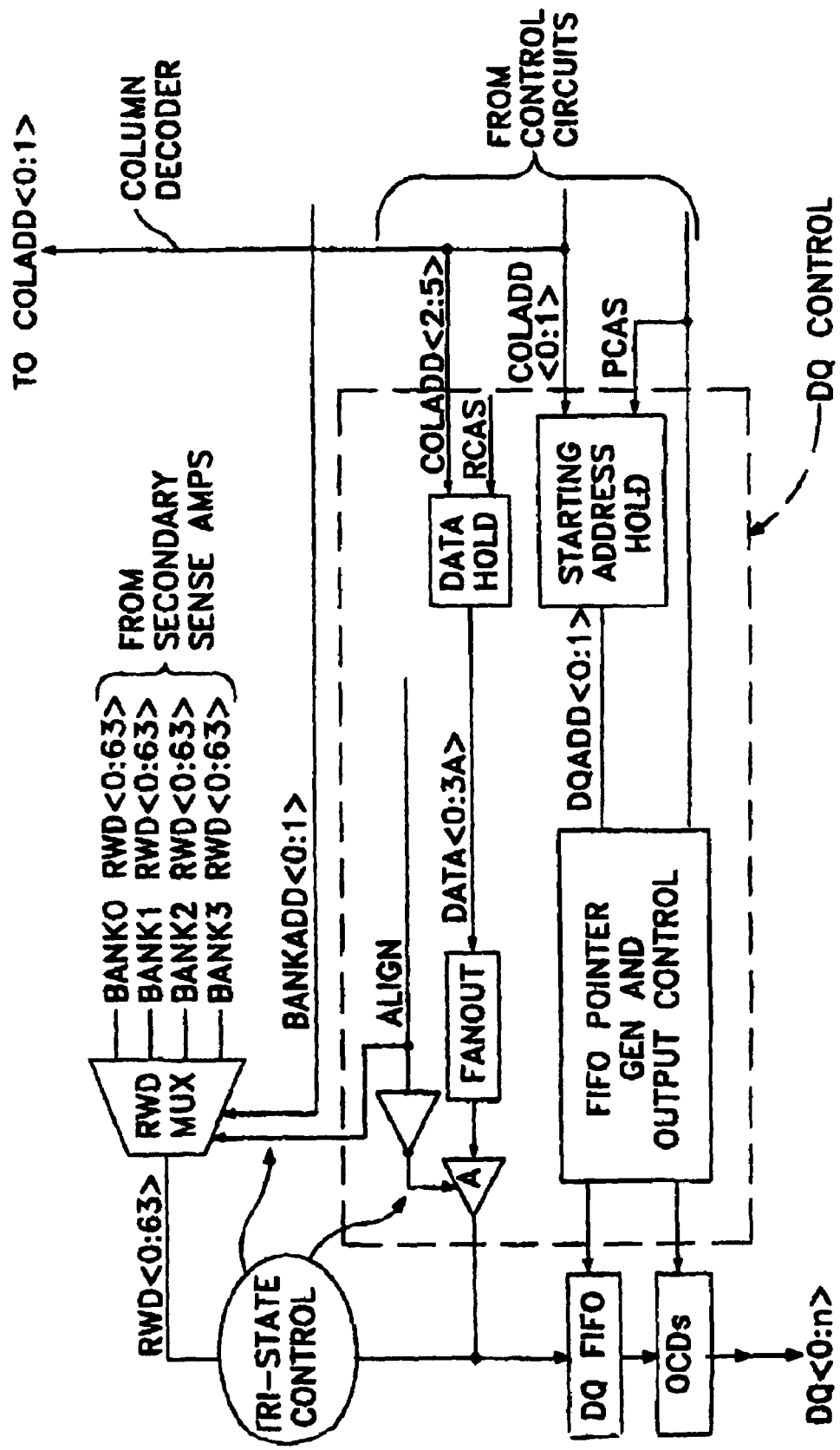
FIG. 11 illustrates an arrangement of adjustment additions to a data path of the type shown in FIG. 10 in the implementation of the principles of the invention in timing calibration, and, FIG. 12 is a timing chart illustrating the conditions produced in timing where adjustment additions are made in a typical data path such as is illustrated in FIG. 11.

In FIG. 11, there is illustrated, in accordance with the invention, an arrangement of adjustment additions to a data path of the typs illustrated that provide the implementation of the principles of the invention. Of particular benefit is the control signal labelled ALIGN that is generated by the DRAM control circuits in response to a mode register set command from the memory controller.

When the ALIGN signal is activated the RWD bus is disconnected from the data array banks and connected to the DATA bus via tri-state control. Data is supplied to the DATA bus via the COLADD bus. This allows the RWD bus to be driven with data from the COLADD bus during a normal "read" operation. The COLADD information is not needed by the column decoder since the data array banks are disconnected from the RWD bus. Therefore any number of consecutive "read" operations may be performed causing any complex sequence of data to be output by the OCDs onto the DQ bus.

It will be noted that the COLADD bus may not be as wide as the RWD bus and therefore a fanout function would facilitate duplication of the data across all bits of the bus. The capability is provided in FIG. 11 in an element labelled FANOUT. The FANOUT function decodes DATA bus information to produce a number of complex vectors. One example of this would be to also drive the complement of the DATA bus such that adjacent OCDs could drive complementary data. Also provided is the ability to use COLADD bits to allow additional unique vectors per "read" operation.

A further illustrative feature is that under a condition where only a subset of OCDs may be required for calibration and in that case an accommodation can be provided for the fact that all RWD lines need not be set to a known state.

The depictions of FIGS. 10 and 11 are illustrative of a synchronous DRAM with a four bit "prefetch" and a fixed burst length of four bits. In a case where the "prefetch" is less than the burst length a counter must be used to issue the data from the element labelled DATA HOLD at the proper time. The starting address DQADD is useful to reorder the burst data in conjunction with a decoding function, for example an element labelled FANOUT resulting in an ability to reduce the width of the DATA bus. As an example, the six patterns 0000, 0001, 0011, 0101, 0111, and 1111 may be used to produce the ten other possible four bit patterns by simply starting the burst from a different address. The starting addrtess DQADD is further useful by being forced into a known state by using the ALIGN signal together with the COLADD bits as a starting address for supplying the data bus.

Figure 12:
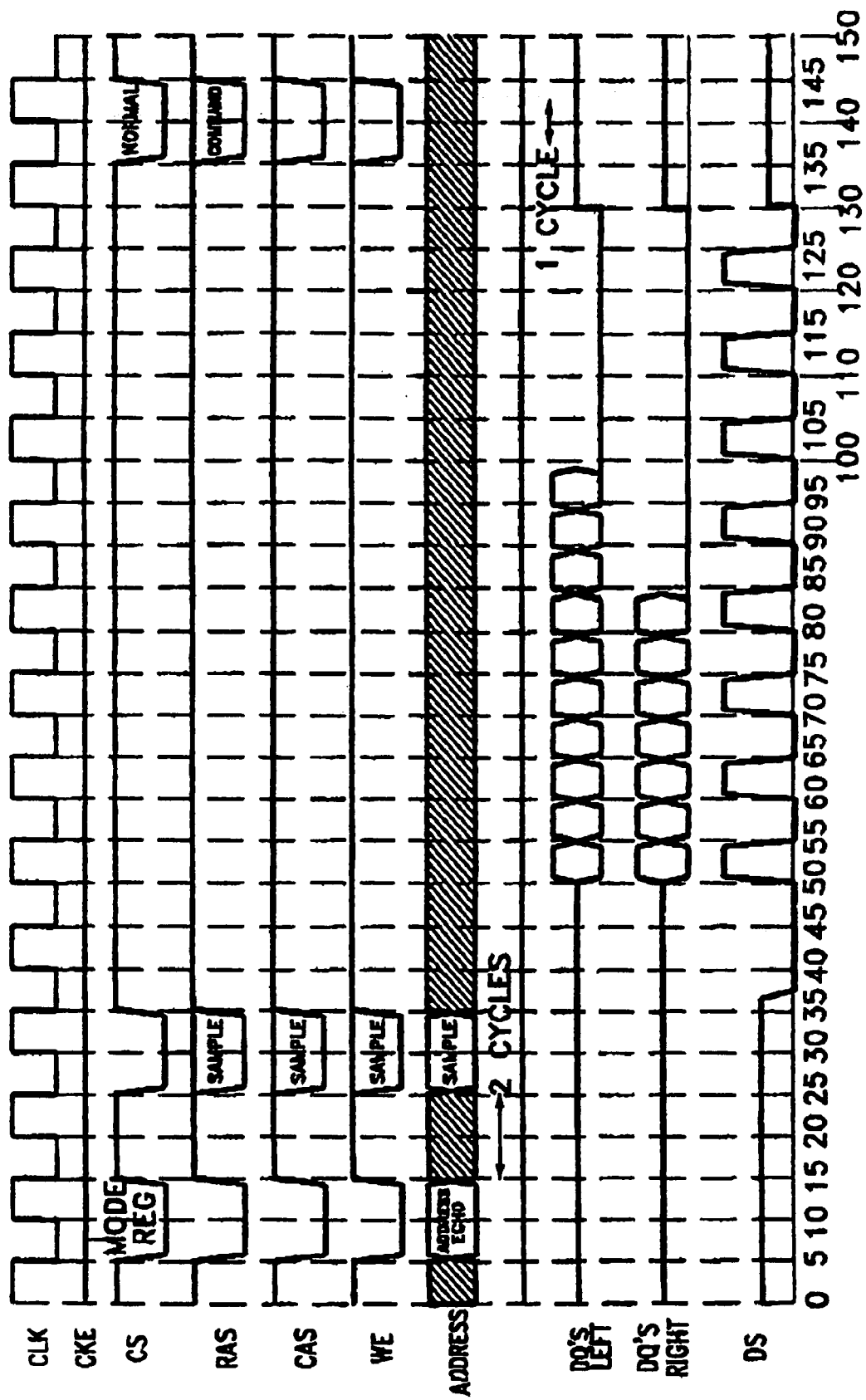

The conditions produced in timing where adjustment additions are made in a typical data path such as is illustrated in FIG. 11 are illustrated in the timing chart of FIG. 12.

Referring to FIG. 11 a protocol for alignment is as follows.

The extended mode register set(EXTMRS), operates to activate the ALIGN mode signal.

The ALIGN mode signal places the RWDMUX in the high impedance mode and the driver A takes control of the RWDs.

Any number of normal "read" commands may follow. In this mode COLADD<0,1>determines the start address and COLADD<2.5> provides the data for the four bit burst.

The extended mode register set deactivates the ALIGN mode signal.

The following observations for assistance in weighing options are set forth.

The drivers involved with the tri-state control labelled A in FIG. 11 may be smaller than would normally be required because with the invention they have the full column to the RWD access time for their level.

Address information is latched with an internal CAS command, PCAS in FIG. 10.

The FANOUT element in FIG. 10 is used to distribute the four bit burst to multiple groups of four RWDs.

The COLADD<0:1> is useable as the first two bits of the four bit burst when the ALIGN mode signal establishes the DQADD<0,1> at a known value.

The COLADD<0:n> is decodable to select one of two predefined burst patterns. FANOUT is useable in generating true and complement data so that adjacent DQ s can switch in opposite directions.

More column addresses such as for example COLADD<6.9> are useable to produce more than one unique four bit burst sequence.

What has been described is a control function for a dynamic random access storage array that selectively can bypass the stored memory and permit the address portion of the data to be diverted for analysis, verification and internal control. The control function can be realized with additional structure and by the selective rerouting through existing structure.

What is claimed is:

1. In data processing apparatus wherein information in processing is arranged with the data having an address portion and a to be stored portion,
the improvement comprising:
   said processing including a selective capability of directing information in said address portion in a separate processing path without disturbing information in said to be stored portion.

2. The improvement of claim 1 wherein said processing includes:
   a separate path in said apparatus for said information address portion, said separate path passing around addressable storage locations for said to be stored information portion, and,
   implementation means adapted to direct said information address portion to said separate path.

3. The improvement of claim 2 further including in said processing, a further processing capability
   said further processing capability being responsive to data arriving at said addressable storage locations through said separate path.

4. The improvement of claim 3 wherein said separate path for said information address portion includes
   address includes address register means for correlation with memory locations in a memory assembly through a serializer with an output buffer, and, said further processing capability including timing register through serializer and output buffer means.

5. The improvement of claim 2 wherein said implementation means operates to disable entry of said to be stored information portion into said memory assembly.

6. In a data processing memory assembly of the type having an input port, an output port, and containing information stored in a plurality of addressable storage locations,
   said memory assembly being responsive in processing to data having an address information portion and a to be stored portion,
the improvement comprising
   said processing including a selective capability of directing said address information portion of said data appearing in a data path to said plurality of addressable storage locations in a separate processing path without disturbing said information stored in said plurality of addressable storage locations.

7. In a data processing memory assembly of the type having an input port, an output port, and containing information stored in a plurality of addressable storage locations,
   said memory assembly being responsive in processing to data having an address information portion and a to be stored portion,
the improvement comprising
   said processing including a selective capability of directing said address information portion of said data appearing in a data path to said plurality of addressable storage locations in a separate processing path without disturbing said information stored in said plurality of addressable storage locations.

8. The improvement of claim 7 wherein said selective capability includes
   a separate address information path around said addressable storage locations to said output port, and,
   a processing instruction implementing the directing of said address information portion of said data to said separate path.

9. The improvement of claim 8 including a data processing capability responsive to data through said separate path delivered to said output port.

10. The improvement of claim 9 wherein said separate address information path is from an address register in said memory assembly through a serializer to an output buffer in said memory assembly, and said processing instruction is from a timing register through a serializer to said output buffer in said memory assembly.

11. The improvement of claim 8 wherein said processing instruction disables entry of to be stored information into said plurality of addressable storage locations.

12. The improvement of claim 8 wherein said processing instruction employs an unused in a standard storage event condition on a terminal in combination with a burst stop command in said memory assembly.

* * * * *